United States Patent [19]

Pittet et al.

[11] 4,400,390
[45] Aug. 23, 1983

[54] METHYL-THIO-2-METHYL-2-PENTENO-ATES

[75] Inventors: Alan O. Pittet, Atlantic Highland; Ranya Muralidhara, Fair Haven; Manfred H. Vock, Locust, all of N.J.

[73] Assignee: International Flavors & Fragrances Inc., New York, N.Y.

[21] Appl. No.: 318,429

[22] Filed: Nov. 5, 1981

[51] Int. Cl.³ .............. C07C 153/023; A61K 31/265
[52] U.S. Cl. .................. 424/301; 260/455 R; 426/535
[58] Field of Search ............. 260/455 R; 424/301; 426/535

[56] References Cited

U.S. PATENT DOCUMENTS

| | | | |
|---|---|---|---|
| Re. 30,363 | 8/1980 | Kratze et al. | 260/454 |
| Re. 30,370 | 8/1980 | Tittet et al. | 260/454 |
| 2,259,869 | 10/1941 | Allen | 260/454 |
| 3,499,769 | 3/1970 | Kratze et al. | 260/454 |
| 3,582,360 | 6/1971 | Proog et al. | 260/454 |
| 3,694,232 | 9/1972 | Hall | 260/454 |
| 3,907,718 | 9/1975 | Hall et al. | 260/454 |
| 3,931,306 | 1/1976 | Hall et al. | 260/454 |
| 3,984,579 | 10/1976 | Hall et al. | 260/454 |
| 4,000,327 | 12/1976 | Tseng et al. | 260/454 |
| 4,041,069 | 8/1977 | Hall et al. | 260/454 |
| 4,098,910 | 7/1978 | Evers et al. | 260/454 |

*Primary Examiner*—Henry R. Jiles
*Attorney, Agent, or Firm*—Arthur L. Liberman

[57] ABSTRACT

Described are cis isomers, trans isomers and mixtures of cis and trans isomers of methyl-thio-2-methyl-2-pentenoate defined according to one of the structures:

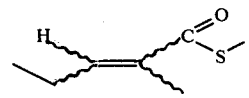

wherein the wavy lines represent "cis" and "trans" configurations of methyl, ethyl and methylthiocarboxy moieties around the carbon-carbon double bond;

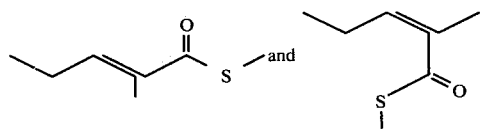

and uses of such methyl-thio-2-methyl-2-pentenoates in augmenting or enhancing the aroma or taste of foodstuffs, chewing gums, medicinal products or toothpastes.

4 Claims, 2 Drawing Figures

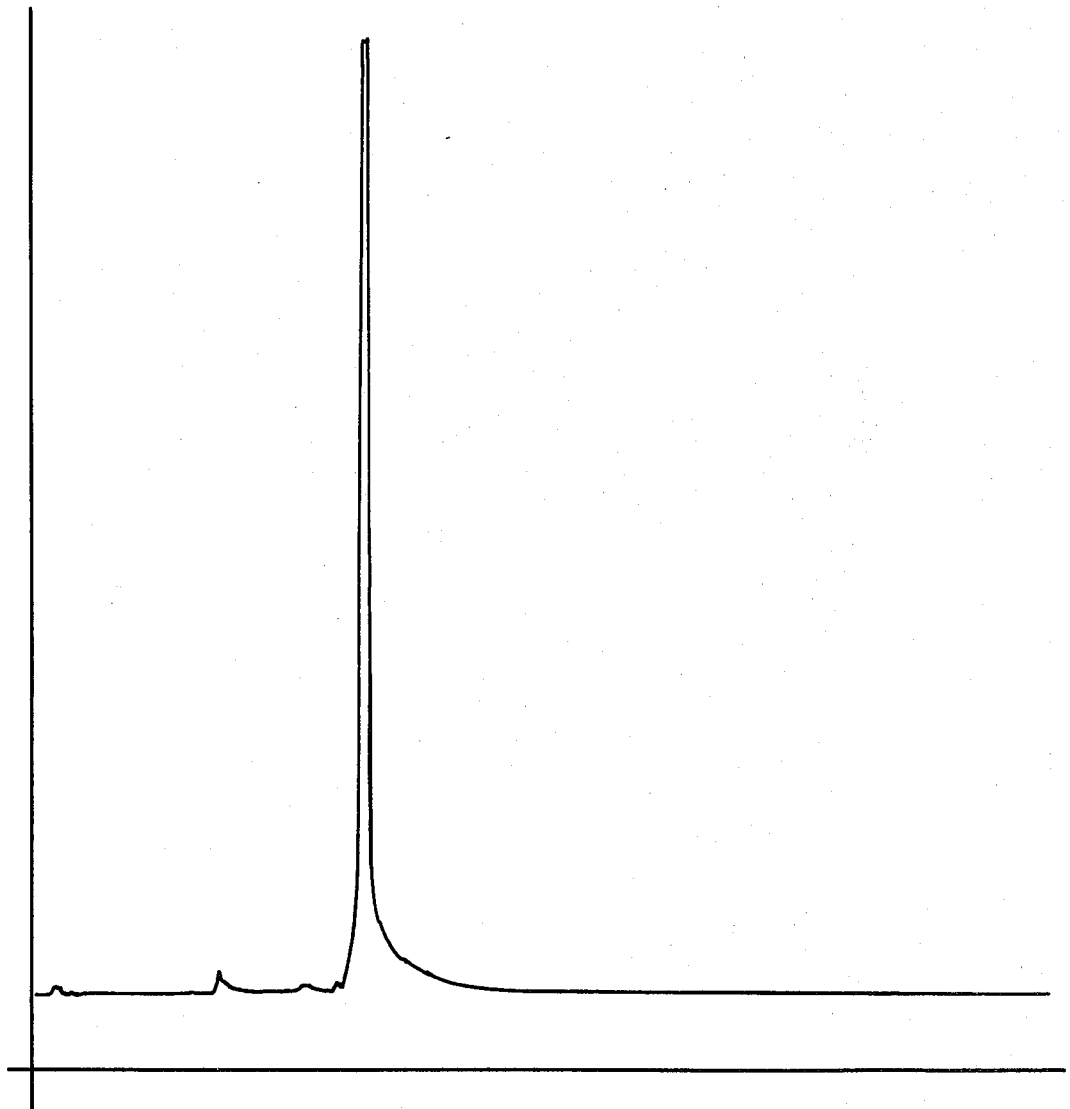

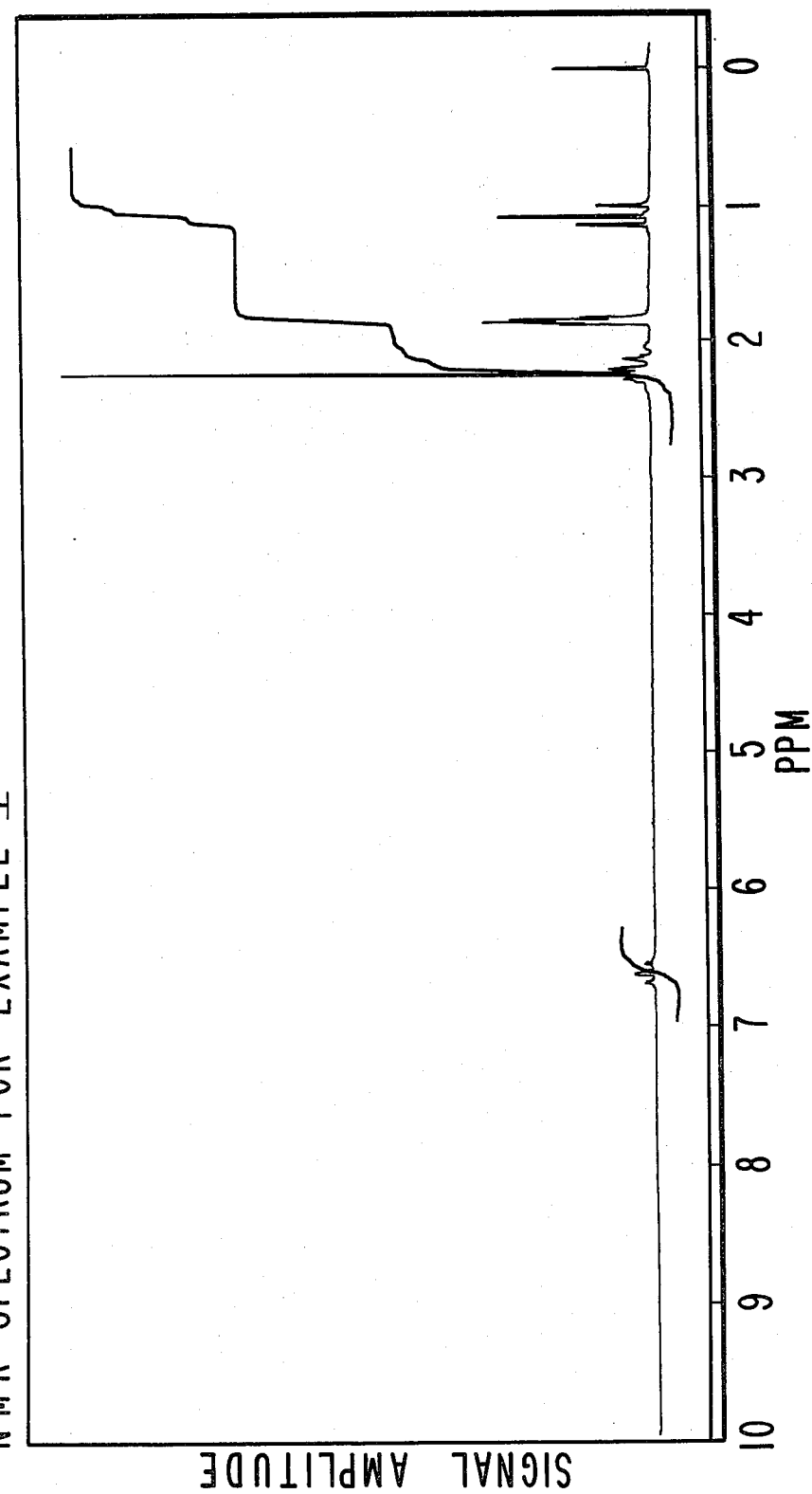

METHYL-THIO-2-METHYL-2-PENTENOATES

BACKGROUND OF THE INVENTION

This invention relates to methyl-thio-2-methyl-2-pentenoate derivatives which are defined according to one of the structures:

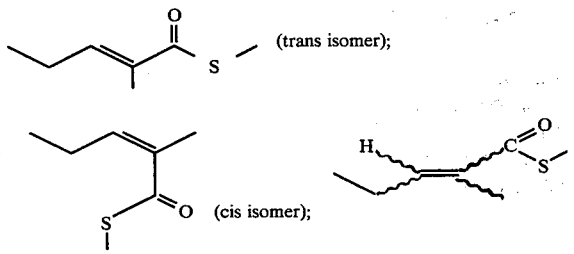

(representative of cis and/or trans isomers) wherein the wavy lines represent moieties juxtaposed around the carbon-carbon double bond, and uses thereof in augmenting or enhancing the aroma or taste of foodstuffs, chewing gums, medicinal products or toothpastes.

Artificial flavoring agents for foodstuffs have received increasing attention in recent years. In many areas, such food flavoring agents have been preferred over natural flavoring agents at least in part due to their diminished cost and their reproducible flavor qualities. For example, natural food flavoring agents such as extracts, concentrates and the like are often subject to wide variations due to changes in the quality, type and treatment of the raw material. Such variations can be reflected in the end product and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods is not completely known. This is noticeable in products having cocoa, chocolate, liver, ripe fruit and strawberry flavor characteristics.

Reproduction of cheesy, surface ripened cheese-like, cocoa powder-like, liver-like and fruity flavor and aroma nuances has been the subject of long and continuing searches by those engaged in the production of foodstuffs and beverages. Thus, severe shortages of food in many parts of the world has given rise to the development of previously unused sources of protein which are unpalatable. Accordingly, the need has arisen for the use of flavoring materials having such aroma and taste nuances which will make such sources of protein palatable to human sensory organs.

Thioesters in particular are well known for use in flavoring of foodstuffs. Thus, U.S. Pat. No. Re. 30,370 discloses compounds having the generic structure:

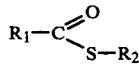

wherein $R_1$ and $R_2$ are alkyl or alkenyl, for example, allyl thiopropionate having the structure:

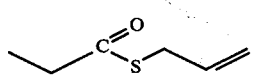

are disclosed as being useful for meaty flavors.

Unsaturated alkenoic acid esters (containing the oxygen rather than the sulfur atom) are also known in augmenting or enhancing the aroma or taste of strawberry flavored foodstuffs, for example, those disclosed in U.S. Pat. No. 3,931,293, for example, the compound having the structure:

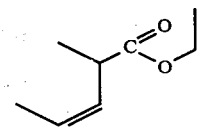

and corresponding trans isomers and mixtures of same having a high "cis" isomer content. Nothing in the prior art discloses the novel compounds of our invention, the methyl-thio-2-methyl-2-pentenoates of our invention or the unexpected, unobvious and advantageous organoleptic uses of same.

BRIEF DESCRIPTION OF THE DRAWINGS

FIG. 1 is the GLC profile for fraction 7 of the distillation product of the reaction product of Example I containing the compounds having the structures:

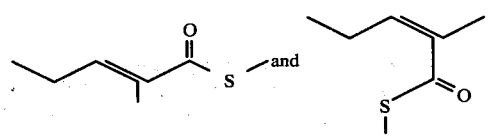

FIG. 2 is the NMR spectrum for peak 1 of the GLC profile of FIG. 1 which is the GLC profile for fraction 7 of the distillation product of the reaction product of Example I containing the compounds having the structures:

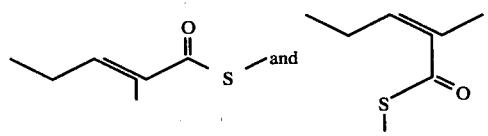

THE INVENTION

It has now been determined that certain methyl-thio-2-methyl-2-pentenoate compounds defined according to one of the structures:

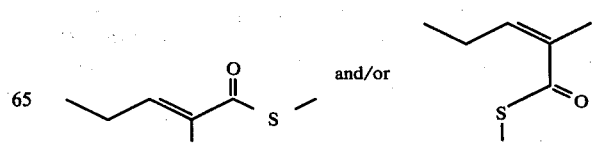

or defined according to the generic structure:

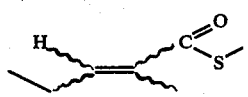

wherein the wavy lines represent "cis" or "trans" configurations of ethyl, methyl, hydrogen or methylthiocarboxy moieties around the carbon-carbon double bond are capable of imparting a variety of flavors to various consumable materials such as foodstuffs, chewing gums, toothpastes and medicinal products.

The compounds of our invention defined according to the structures:

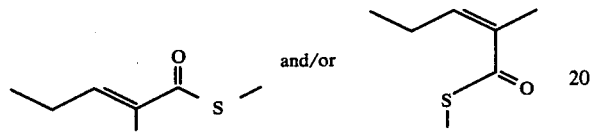

are useful in augmenting or enhancing the aroma and/or taste of foodstuffs having cocoa, chocolate, liver, ripe fruity and/or strawberry flavors.

The compounds of our invention defined according to one or both of the structures:

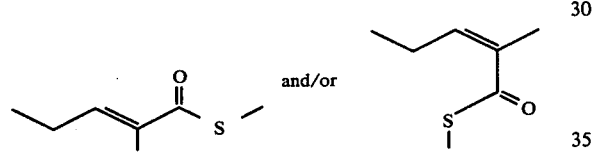

may be prepared by first reacting 2-methyl-2-pentenoic acid (the cis or trans isomers or mixtures of the cis and trans isomers as desired) defined according to one of the structures:

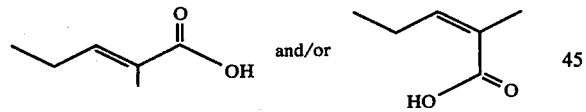

with a halogenating agent defined according to the structure:

ZX$_n$ wherein Z represents phosphorous, phosphorous oxy having the structure:

≡P=O]

or sulfoxy having the structure:

=[S=O]

wherein n is the integer 2, 3 or 5; wherein X represents chloro or bromo; wherein n is 3 or 5 when Z represents phosphorous; n is 3 when Z represents phosphorous oxy having the structure:

≡P=O]

and n is 2 when Z is sulfoxy having the structure:

=[S=O]

to form the alkenoyl halide defined according to the structure:

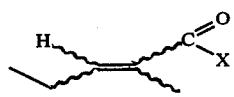

wherein the wavy lines are defined as above.

The resulting alkenoyl halide or mixture of cis and trans alkanoyl halides is then reacted with methyl mercaptan in order to form the compounds of our invention defined according to the structures:

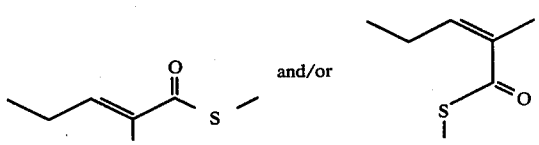

or defined according to the structure:

wherein the wavy lines are defined supra.

The reaction defined above may be graphically illustrated as follows:

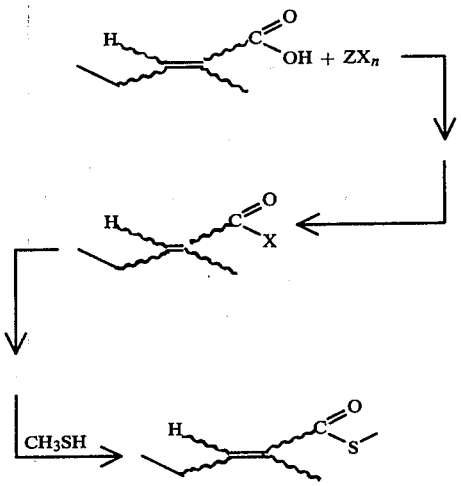

The reaction of the 2-methyl-2-pentenoic acid defined according to the structure:

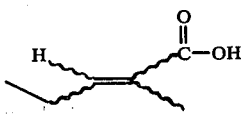

with the compound defined according to the structure:

ZX$_n$ for example, thionyl chloride (SOCl₂) phosphorous pentachloride, phosphorous oxychloride (POCl₃) or phosphorous trichloride takes place in the presence of an inert solvent such as toluene or benzene or xylene at reflux conditions. Thus, in the case of using a toluene solvent, it is preferable that the reaction be carried out at a temperature in the range of 50°-110° C. depending on the quantity of toluene in the reaction mass, preferably and expeditiously the reaction takes place at atmospheric pressure although pressures greater than atmospheric may be used with higher temperatures of reaction and shorter time periods of reaction. Preferably the mole ratio of the compound having the structure:

ZX$_n$:the 2-methyl-2-pentenoic acid having the structure:

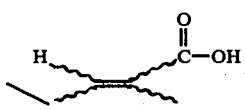

is 1:1. In order to insure that all of the 2-methyl-2-pentenoic acid is reacted, a slight excess of the compound having the structure:

ZX$_n$ may be used. Thus, if thionyl chloride, phosphorous oxychloride, phosphorous trichloride or phosphorous pentachloride is used and a slight excess of same is used, the excess phosphorous trichloride, phosphorous oxychloride, phosphorous pentachloride or thionyl chloride may subsequently be hydrolyzed or neutralized after the second reaction of the alkenoyl halide having the structure:

with methyl mercaptan.

Thus, in the reaction of methyl mercaptan with the alkenoyl halide having the structure:

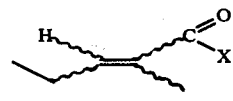

wherein X is chloro or bromo, it is preferable that the reaction temperature be between −10° C. and 0° C. It is also preferable that the mole ratio of methyl mercaptan:alkenoyl halide defined according to the structure:

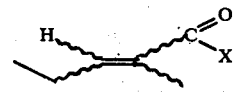

be about 1:1 and if any excess of any reagent is used, that excess be in favor of the methyl mercaptan. The reaction between the methyl mercaptan and alkenoyl halide defined according to the structure:

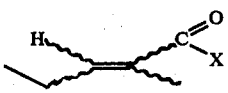

also is to take place in the presence of an inert solvent such as benzene, toluene or xylene. Conveniently, the same solvent as used in the first reaction between the compound having the structure:

ZX$_n$ and the 2-methyl-2-pentenoic acid having the structure:

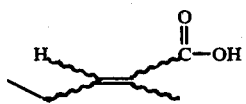

is used. Thus, if toluene is used in the first reaction, then conveniently, the same toluene may be used in the second reaction.

At the end of the reaction, the reaction mass is heated up in order to evolve any excess volatiles, e.g. excess methyl mercaptan and in order to evolve products of reaction, e.g. hydrogen chloride, sulfur dioxide or the like.

The reaction mass is then "worked up" by first cooling to room temperature and when washing the reaction mass with water and finally drying over an anhydrous inert drying agent such as anhydrous sodium sulfate. The reaction mass is then distilled to yield product distilling at a vapor temperature of about 95°-98° C. and a pressure of 5 mm/Hg or an equivalent distillation temperature and pressure.

It will thus be appreciated from the present disclosure that the methyl-thio-2-methyl-2-pentanoates of our invention can be used to alter, vary, fortify, modify, enhance or otherwise improve the flavor of a wide variety of materials which are ingested, consumed or otherwise organoleptically sensed.

The term "alter" in its various forms will be understood herein to mean the supplying or imparting of a flavor character or note to an otherwise bland, relatively tasteless substance, or augmenting an existing flavor characteristic with the natural flavor is deficient in some regard or supplementing the existing flavor impression to modify the organoleptic character.

Such compounds are, accordingly, useful in flavoring compositions. A flavoring composition is taken to mean one which contributes a part of the overall flavor impression by supplementing or fortifying a natural or artificial flavor in a material or one which supplies substantially all the flavor and/or aroma character to a consumable article.

The term "enhance" is intended herein to mean the intensification of a particular aroma or taste nuance without changing the quality or nature of said nuance and without adding an additional aroma or taste nuance to the consumable material, the organoleptic properties of which are enhanced.

The term "foodstuff" as used herein includes both solid and liquid ingestible material for man or animals, which materials usually do, but need not, have nutritional value. Thus, the term "foodstuff" includes meats, gravies, soups, convenience foods, malt, alcoholic and other beverages, milk and dairy products, seafoods including fresh, crustaceans, mollusks and the like, candies, vegetables, cereals, soft drinks, snacks, dog and cat food, other veterinary products, cattle feed and the like.

When the methyl-thio-2-methyl-2-pentenoates of our invention are used in a flavoring composition, they can be combined with conventional flavoring materials or adjuvants. Such co-ingredients or flavoring adjuvants are well known in the art for such use and have been extensively described in the literature. Apart from the requirement that any such adjuvant material be ingestibly acceptable and thus non-toxic or otherwise non-deleterious, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols; esters including 2-methyl-2-pentenoic acid esters, 2-methyl-3-pentanoic acid esters and the like; carbonyl compounds including ketones and aldehydes such as maltol and ethyl maltol; lactone; other cyclic organic materials including benzene derivatives, alicyclic compounds, heterocyclics such as furans, pyrazines and the like; sulfur-containing materials other than the instant sulfur containing materials including thiols, sulfides, disulfides and the like; proteins, lipids, carbohydrates; so-called flavor potentiators such as monosodium glutamate, guanylates, inosinates; natural flavoring materials such as cocoa, vanilla, strawberry essence, and caramel; essential oils and extracts such as anise oil, clove oil and the like and artificial flavoring materials such as vanillin, 2-methyl-2-pentanoic acid, ethyl-2-methyl-3-pentenoate, maltol, ethyl maltol and the like.

Specific flavor adjuvants are as follows:
2-methyl-2-pentenoic acid (cis and/or trans isomers)
ethyl-2-methyl-3-pentenoic (cis and/or trans isomers)
ethyl-2-methyl butyrate
maltol
ethyl maltol
vanillin
butyl valerate
2,3 diethyl pyrazine
methyl cyclopentenolone
benzaldehyde
strawberry essence
valerian oil Indian
propylene glycol
2-phenyl-4-pentenal
3-phenyl-4-pentenal
2-phenyl-5-hexenal
2-phenyl-4-hexenal
2,5-dimethyl-3-hydroxy delta$^{2,3}$ furan-4-one
2-methyl-5-ethyl-3-hydroxy dihydro delta$^{2,3}$ furan-4-one
methyl tiglate
methyl angelate
beta dimascone
beta damascenone
alpha damascone
trans,trans delta damascone
dimethoxy phenol
amyl acetate
amyl cinnamate
gamma butyrolactone
furfural
acetaldehyde
trimethyl pyrazine
phenyl acetic acid
isovaleraldehyde
ethyl vanillin
cocoa extract
isobutyraldehyde
benzyl alcohol
methyl sulfide
methyl disulfide
isobutyl acetate
isoamyl acetate
phenylethyl acetate
diacetyl
acetophenone
isoamyl alcohol
phenylethyl alcohol
2-methyl pyrazine
2,6-dimethyl pyrazine
2,3,5,6-tetramethyl pyrazine
3-phenyl-3-pentenal
3-(2'-methylphenyl)-4-pentenal
3-phenyl-4-methyl-4-pentenal
3-(2',3',4'-trimethoxyphenyl)-4-methyl-4-pentenal
oil of cumin
oil of mustard
oil of celery
oil of ginger
oil of cloves
oil of coriander
oil of pimenta berries
oil of black pepper
oleoresin capsicum
oil of nutmeg
p-hydroxybenzylacetone
ethyl methylphenyl glycidate
benzyl acetate
ethyl butyrate
methyl cinnamate
methyl anthranilate
alpha-ionone
gamma undecalactone
anethole
cis-3-hexenol and
propylene glycol.

When used in conjunction with foodstuffs, the methyl-thio-2-methyl-2-pentenoates of our invention yield cheesy, surface ripened cheese-like, cocoa powder-like, liver-like and fruity aroma and flavor nuances causing this material to be useful in cocoa, chocolate, liver, ripe fruit and strawberry flavored foodstuffs. When used as such, the concentration of the methyl-thio-2-methyl-2-pentenoate derivatives of our invention whether cis isomers, trans isomers or mixtures of cis and trans isomers may be used in concentrations of from about 0.5 ppm up to about 100 ppm, most preferably between 3 and 20 ppm.

Also useful as food flavor adjuvants together with the methyl-thio-2-methyl-2-pentenoates of our invention are the food flavor adjuvants specifically set forth and exemplified in the following U.S. Pat. Nos. the disclosures of which are incorporated herein by reference: 3,582,360, 3,694,232, RE. 30,370, 4,000,327, 3,931,306, 3,984,579, 3,907,718, 4,041,069, 3,499,769, RE. 30,363, 4,098,910.

The following Example I is given to illustrate a technique for producing the methyl-thio-2-methyl-2-pentenoate derivatives of our invention. The following Examples II and onwards are given to illustrate embodiments of our invention as it is presently preferred to practice it with respect to the organoleptic utilities of the methyl-thio-2-methyl-2-pentenoate derivatives of our invention.

It will be understood that these examples are illustrative and the invention is not to be considered restricted thereto except as indicated in the appended claims.

EXAMPLE I

PREPARATION OF METHYL-THIO-2-METHYL-2-PENTENOATES

Reactions:

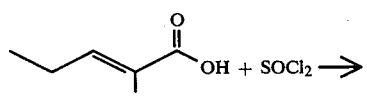

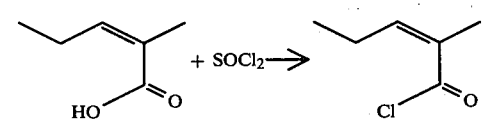

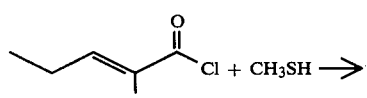

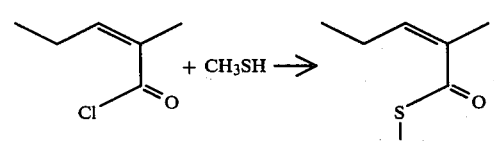

Into a 2 liter reaction flask equipped with heating mantle, cooling bath, stirrer, thermometer, addition funnel, reflux condenser, nitrogen blanket apparatus, dry trap and caustic trap for recovery of hydrogen chloride and sulfur dioxide gasses are placed 200 ml toluene followed by 150 grams (1.82 moles) of 2-methyl-2-pentenoic acid.

While maintaining the temperature of the resulting mixture at 23° C. over a period of 20 minutes, 173 grams (1.45 moles) of thionyl chloride is added to the reaction mass.

The reaction mass is then slowly heated to reflux and while refluxing the reaction mass over a period of 1 hour while maintaining the temperature at 62°-63° C., a small amount of hydrogen chloride and sulfur dioxide is evolved.

At the end of the 1 hour period, GLC analysis indicates the completion of the reaction. The reaction mass is then cooled to −5° C.

While maintaining the reaction mixture at a temperature of −4°-−5° C., 104 grams (2.20 moles) of methyl mercaptan is added to the reaction mixture over a period of 30 minutes. At the end of the addition of the methyl mercaptan, the reaction mass is heated to room temperature (24° C.). Excess methyl mercaptan is then evolved. The reaction mass is heated at 30° C. for a period of 1 hour.

The reaction mass is then added to a separatory funnel containing 250 ml of water and the phases are allowed to separate.

The organic phase is then washed with an additional 250 ml of water. The organic phase is then dried over anhydrous sodium sulfate and the resulting mixture is then filtered and distilled on a 1" Goodloe column yielding the following fractions:

| Fraction Number | Vapor Temp. (°C.) | Liquid Temp. (°C.) | Pressure mm/Hg. |
|---|---|---|---|
| 1 | 25/35 | 35/61 | 7/10 |
| 2 | 51 | 75 | 7 |
| 3 | 67 | 88 | 7 |
| 4 | 73 | 94 | 7 |
| 5 | 91 | 105 | 5 |
| 6 | 96 | 138 | 5 |
| 7 | 90 | 180 | 5 |

Fractions 6 and 7 are bulked and evaluated for their organoleptic properties.

Bulked fractions 6 and 7 have a cheesy, surface ripened cheese-like, cocoa powder-like, liver-like and fruity aroma and flavor profile making it useful in cocoa, chocolate, liver, ripe fruit and strawberry aroma. The bulked fractions 6 and 7 are a mixture of cis and trans isomers having the structures:

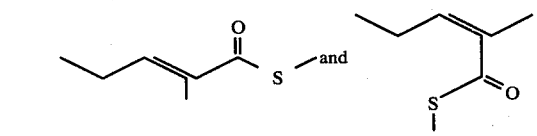

as confirmed by NMR, IR and mass spectral analyses.

FIG. 1 is the GLC profile for fraction 7. Peak "1" on FIG. 1 represents a mixture of cis and trans isomers having the structures:

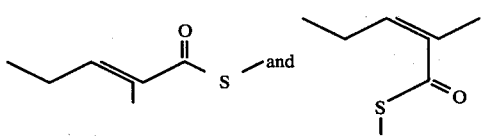

FIG. 2 is the NMR spectrum for peak "1" of the GLC profile of FIG. 1.

EXAMPLE II

The following chocolate basic formulation is prepared:

| Ingredients | Parts by Weight |
|---|---|
| Dimethoxy phenol (10% in propylene glycol) | 0.5 |
| Amyl acetate | 0.1 |
| Amyl cinnamate | 0.1 |
| Gamma butyryl lactone | 0.2 |
| Furfural | 0.05 |
| Benzaldehyde | 0.05 |
| Trimethyl pyrazine | 0.05 |
| Phenyl acetic acid | 0.35 |
| Isovaleraldehyde | 1.6 |
| Ethyl maltol | 12.0 |

| Ingredients | Parts by Weight |
|---|---|
| Ethyl vanillin | 20.0 |
| 1,3-propylene glycol USP | 165.0 |
| Nestle cocoa extract | 800.0 |

This basic chocolate flavor is divided into two parts. To the first part is added at the rate of 2 ppm the methyl-thio-2-methyl-2-pentenoate, cis and trans isomer mixture, prepared according to Example I. To the second part nothing is added. Both flavors are compared at the rate of 200 ppm. The flavor with the ingredient of Example I has additional very characteristic cocoa powder-like notes both in aroma and taste. These notes are completely missing in the basic chocolate flavor that does not contain the additional methyl-thio-2-methyl-2-pentenoate prepared according to Example I. Therefore, the flavor with the material of Example I is preferred as having the desired cocoa powder characteristic.

EXAMPLE III

COCOA FLAVOR FORMULATION

The following cocoa flavor formulation is prepared by admixing the following ingredients:

| Ingredients | Parts by Weight |
|---|---|
| Maltol | 3 |
| Acetaldehyde (50% in ethanol) | 20 |
| Isobutyraldehyde | 16 |
| Isovaleraldehyde | 43 |
| Benzyl alcohol | 10 |
| Methyl sulfide | 0.4 |
| Methyl disulfide | 0.4 |
| Isobutyl acetate | 0.1 |
| Isoamyl acetate | 0.2 |
| Phenylethyl acetate | 0.6 |
| Diacetyl (10% in ethanol) | 0.2 |
| Acetophenone | 1.0 |
| Furfural (50% in ethanol) | 0.1 |
| Benzaldehyde | 1.0 |
| Isoamyl alcohol | 0.2 |
| Phenylethyl alcohol | 3.5 |
| Gamma butyrolactone | 0.2 |
| 2-methyl pyrazine | 0.5 |
| 2,6-dimethyl pyrazine | 4.0 |
| 2,3,5,6-tetramethyl pyrazine | 0.2 |
| 3-phenyl-3-pentenal | 0.5 |
| 3(2'-methylphenyl)4-pentenal | 3.4 |
| 3-phenyl-4-methyl-4-pentenal | 4.2 |
| 3-(2',3',4'-trimethoxyphenyl)-4-methyl-4-pentenal | 0.4 |

A flavor composition is prepared by adding a 1.9 solution of the above cocoa flavor formulation in propylene glycol/ethyl alcohol (V/V80/20), vanillin in the ratio of 10 grams per kilogram of solution.

To this formulation at the rate of 50 ppm is added the methyl-thio-2-methyl-2-pentenoate prepared according to Example I (bulked fractions 6 and 7).

The resulting flavor is found to have excellent sweet, dark, cocoa powder-like and milk chocolate-like nuances with a pleasant nutty after taste.

EXAMPLE IV

The formulation of Example II is added to a commercially available chocolate flavored dessert containing skim milk, sugar, non-faty dairy milk solids and cocoa with a bland, thin cocoa flavor. The addition of 45 mg/kg of the resulting formulation of Example III increases the sweet, milk chocolate, cocoa powder-like and nut-like notes to a desirable level and improves the overall flavor.

EXAMPLE V

Methyl-thio-2-methyl-2-pentenoate produced according to Example I is added to a commercially available chocolate flavored dessert containing skim milk, sugar, non-fat dry milk solids and cocoa with a bland, thin cocoa note. The addition at a rate of 0.5 ppm of the methyl-thio-2-methyl-2-pentenoate to this cocoa flavor causes the resulting dessert to have an excellent cocoa powder taste and a more pleasant mouth feel.

EXAMPLE VI

The following ground sausage mixture is prepared:

| Ingredients | Parts by Weight |
|---|---|
| Ground beef | 200 |
| Beef suet | 120 |
| Ice/NaCl (50:50 mixture) | 200 |
| Potato flour | 100 |
| Anhydrous bread crumbs | 140 |
| Dry milk powder | 20 |
| Standard spice flavor containing: | 10 |
| Oil of cumin | 1.6 |
| Oil of mustard | 3.3 |
| Oil of celery | 3.3 |
| Oil of ginger | 5.2 |
| Oil of cloves | 14.3 |
| Oil of coriander | 17.6 |
| Oil of pimenta berries | 22.0 |
| Oil of black pepper | 43.0 |
| Oleoresin capsicum | 373.0 |
| Oil of nutmeg | 500.0 |

To the above mixture 0.02% by weight of the following mixture is added:

| Ingredients | Parts by Weight |
|---|---|
| Methyl-thio-2-methyl-2-pentenoate prepared according to Example I (bulked fractions 6 and 7) | 5 |
| Ethyl alcohol (95% food grade) | 95 |

The resulting mixture is then formed into a sausage and encased in the usual manner. The encased sausage is heated in water at a temperature of 160°–180° F. for a period of two hours. The sausage has a liver-like taste reminiscent of the taste of sausage made with natural liver.

The resultant natural liver flavor is enhanced even further when instead of essentially pure methyl-thio-2-methyl-2-pentenoate prepared according to Example I, a 50:50 mixture (weight:weight) of 1 part methyl-thio-2-methyl-2-pentenoate and 1 part n-propyl(2-methyl-3-furyl)disulfide prepared according to Examples V, VI or X of U.S. Pat. No. 4,098,910 issued on July 4, 1978 (the disclosure of which is incorporated herein by reference) is added to the sausage.

EXAMPLE VII

The following basic strawberry flavor is prepared:

| Ingredients | Parts by weight |
|---|---|
| p-hydroxybenzylacetone | 2 |
| Vanillin | 15 |

-continued

| Ingredients | Parts by weight |
| --- | --- |
| Maltol | 20 |
| Ethyl methylphenyl glycidate | 15 |
| Benzyl acetate | 20 |
| Ethyl butyrate | 10 |
| Methyl cinnamate | 5 |
| Methyl anthranilate | 5 |
| Alpha-ionone | 1 |
| Gamma-undecalactone | 2 |
| Diacetyl | 2 |
| Anethole | 1 |
| Cis-3-hexenol | 17 |
| Ethanol (95% aqueous food grade) | 385 |
| Propylene Glycol | 500 |

To one-third of this flavor, the methyl-thio-2-methyl-2-pentenoate (bulked fractions 6–7) prepared according to Example I is added at the rate of 1%. To another third of this flavor, a 50:50 mixture of substantially pure ethyl-2-methyl-cis-3-pentenoate prepared according to Example XLII of U.S. Pat. No. 4,000,327 issued on Dec. 28, 1976 and methyl-thio-2-methyl-2-pentenoate prepared according to Example I bulked fractions 6–7) is added at the rate of 1%. The third portion of this flavor is kept "as is". The three flavors thus produced are compared at the rate of 0.005% (50 ppm) in water by a bench panel.

The flavors containing the methyl-thio-2-methyl-2-pentenoate and containing the 50:50 mixtures of methyl-thio-2-methyl-2-pentenoate and ethyl-2-methyl-cis-3-pentenoate are found to have more fresh, natural, strawberry-like aromas and tastes than the basic flavor formulation and is preferred over the basic formulation.

EXAMPLE VIII

The following concentrates are prepared:

| Ingredients | Parts by Weight |
| --- | --- |
| A. Geraniol | 1.0 |
| Ethyl methyl phenyl glycidate | 3.5 |
| Methyl-thio-2-methyl-2-pentenoate | 5.0 |
| Vanillin | 5.5 |
| Ethyl pelargonate | 13.0 |
| Isoamyl acetate | 14.0 |
| Ethyl butyrate | 58.0 |
| B. A second concentrate is prepared as follows: | |
| Naphthyl ethyl ether | 1.0 |
| Vanillin | 2.5 |
| Ethyl methyl phenyl glycidate | 3.0 |
| Methyl-thio-2-methyl-2-pentenoate | 5.0 |
| Ethyl acetate | 9.5 |
| Isoamyl acetate | 12.0 |
| Ethyl butyrate | 26.0 |
| Isoamyl butyrate | 41.0 |

The concentrate prepared in Part "A" is dissolved in 4 volumes of propylene glycol and the mixture is added to a hard candy melt at the rate of 1.5 ounces of the concentrate solution per 100 pounds of melt. After the finished candy has been produced, it is found to have an excellent strawberry flavor. When the candy is compared with the candy made under the same conditions but without the methyl-thio-2-methyl-2-pentenoate prepared according to the process of Example I, supra in the concentrate, it is found to have an inferior strawberry flavor.

The propylene glycol solution of the concentrate as prepared in Part "B" is added to a simple syrup at the rate of ⅛ ounce per gallon of syrup. The syrup is acidified by the addition of 1.5 ounces of 50% aqueous citric acid solution to each gallon of syrup. A carbonated beverage is prepared by admixing 1 ounce of the flavored acidified syrup with 5 ounces of carbonated water. The beverage so prepared has an excellent fresh, strawberry flavor and is found to be markedly superior to a beverage prepared in the same manner but without the mixture containing the methyl-thio-2-methyl-2-pentenoate prepared according to Example I.

The flavor concentrate of Part "A" is admixed with gum arabic and in the proportion of 7 pounds of concentrate to 28 pounds of gum arabic in 65 pounds of water, and the aqueous mixture is spray-dried. The flavor concentrate-carrier combination so obtained is then added to a gelatin dessert mix in the ratio of 1 ounce of spray dried material to 100 pounds of dessert mix powder. The gelatin dessert produced from the mix has an excellent strawberry flavor and is markedly superior to a gelatin dessert prepared in the same manner without the mixture containing the methyl-thio-2-methyl-2-pentenoate (bulked fractions 6–7) prepared according to Example I in the concentrate.

EXAMPLE IX

A. Powder Flavor Composition 20 grams of the flavor composition of Example VII is emulsified in a solution containing 300 grams gum acacia and 700 grams of water. The emulsion is spray-dried with a Bowen Lab Model Drier utilizing 260 c.f.m. of air with an inlet temperature of 500° F. and an outlet temperature of 500° F. and a wheel speed of 50,000 rpm.

B. Sustained Release Flavor

The following mixture is prepared:

| Ingredients | Parts by Weight |
| --- | --- |
| Strawberry flavor composition of Example VII | 20 |
| Propylene glycol | 9 |
| Cab-O-Sil ® M-5 (Brand of silica produced by the Cabot Corporation of 125 High St., Boston, Mass. 02110 Physical properties: Surface area: 200 m²/gm. Nominal particle size: 0.012 microns Density: 2.3 lbs/cu.ft.) | 5 |

The Cab-O-Sil ® is dispersed in the liquid strawberry flavor composition of Example VII with vigorous stirring thereby resulting in a viscous liquid. 71 parts by weight of the powder flavor composition of Part "A" supra is then blended into said viscous liquid with stirring at 25° C. for a period of 30 minutes resulting in a dry, free-flowing sustained release flavor powder.

EXAMPLE X 10 parts by weight of 50 Bloom pigskin gelatin is added to 90 parts by weight of water at a temperature of 150° F. The mixture is agitated until the gelatin is completely dissolved and the solution is cooled to 120° F. 20 parts by weight of the liquid flavor composition of Example VII is added to the solution which is then homogenized to form an emulsion having a particle size in the range of 5–40 microns. This material is kept at 120° F. under which conditions the gelatin will not jell.

Coacervation is induced by adding, slowly and uniformly, 40 parts by weight of a 20% solution of sodium sulfate. During coacervation, the gelatin molecules are deposited uniformly about each oil droplet as a nucleus.

Gelation is effected by pouring the heated coacervate mixture into 1,000 parts by weight of 7% aqueous solution of sodium sulfate at 65° F. The resulting jelled coacervate may be filtered and washed with water at temperatures below the melting point of gelatin to remove the salt.

Hardening of the filter cake, in this example, is effected by washing with 200 parts by weight of 37% solution of formaldehyde in water. The cake is then thoroughly washed to remove the residual formaldehyde.

EXAMPLE XI

CHEWING GUM 100 parts by weight of chicle are mixed with 4 parts by weight of the flavor prepared in accordance with Example IX. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting, sweet strawberry flavor.

EXAMPLE XII

CHEWING GUM 100 parts by weight of chicle are mixed with 18 parts by weight of the flavor prepared in accordance with Example IX. 300 parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting -trawberry flavor.

EXAMPLE XIII

TOOTHPASTE FORMULATION

The following separate groups of ingredients are prepared:

| Parts by Weight | Ingredient |
|---|---|
| Group "A" | |
| 30.200 | Glycerine |
| 15.325 | Distilled water |
| .100 | Sodium benzoate |
| .125 | Saccharin Sodium |
| .400 | Stannous fluoride |
| Group "B" | |
| 12.500 | Calcium carbonate |
| 37.200 | Dicalcium phosphate (Dihydrate) |
| Group "C" | |
| 2.000 | Sodium n-lauroyl sarcosinate (foaming agent) |
| Group "D" | |
| 1.200 | Flavor material of Example IX |
| 100.00 (total) | |

Procedure:
1. The ingredients in Group "A" are stirred and heated in a steam jacketed kettle to 160° F.
2. Stirring is continued for an additional three to five minutes to form a homogeneous gel.

3. The powders of Group "B" are added to the gel, while mixing until a homogeneous paste is formed.
4. With stirring, the flavor of "D" is added and lastly, the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure, yields a pleasant strawberry flavor of constant strong intensity throughout said procedure (1–1.5 minutes).

EXAMPLE XIV

CHEWABLE VITAMIN TABLETS

The flavor material produced according to the process of Example IX is added to a chewable vitamin tablet formulation at a rate of 10 grams per kilogram which chewable vitamin formulation is prepared as follows:

In a Hobart mixer the following materials are blended to homogeneity:

| | Gms/1000 Tablets |
|---|---|
| Vitamin C (ascorbic acid) as ascorbic acid-sodium ascorbate mixture 1:1 | 70.0 |
| Vitamin B$_1$ (thiamine mononitrate) as Rocoat ® thiamine mononitrate 33⅓% Hoffman La Roche) | 4.0 |
| Vitamin B$_2$ (riboflavin) as Rocoat ® riboflavin 33⅓% | 5.0 |
| Vitamin B$_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example IX | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 grams dry Vitamin A acetate and 0.6 grams Vitamin D are then added as beadlets. The entire blend is then compressed using concave punches at 0.5 grams each.

Chewing of the resultant tablets yields a pleasant long-lasting, consistently strong strawberry flavor for a period of 12 minutes.

What is claimed is:
1. Methyl-thio-2-methyl-2-pentenoate defined according to the structure:

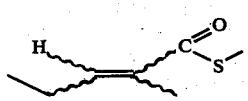

wherein the wavy lines represent covalent bonds juxtaposed in a "cis" or "trans" configuration around the carbon-carbon double bond of the structure.

2. The compound of claim 1 having the structure:

3. The compound of claim 1 having the structure:
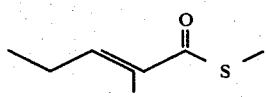
4. A mixture of compounds having the structures:
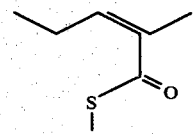
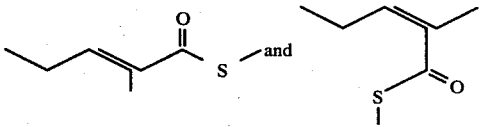
* * * * *